United States Patent [19]

Hüttinger

[11] 4,420,410

[45] Dec. 13, 1983

[54] PERSONAL CARE CLEANSING AGENT

[75] Inventor: Rudolf Hüttinger, Essen, Fed. Rep. of Germany

[73] Assignee: Th. Goldschmidt AG, Essen, Fed. Rep. of Germany

[21] Appl. No.: 299,184

[22] Filed: Sep. 3, 1981

[30] Foreign Application Priority Data

Sep. 10, 1980 [DE]  Fed. Rep. of Germany ....... 3033929

[51] Int. Cl.$^3$ .............. C11D 1/90; C11D 7/26; A61K 7/06
[52] U.S. Cl. .................. 252/117; 252/89.1; 252/154; 252/155; 252/173; 252/546; 252/550; 252/551; 252/DIG. 13; 252/DIG. 14; 424/70; 424/312; 424/365
[58] Field of Search .............. 252/546, 550, 551, 173, 252/89.1, 154, 155, DIG. 13, DIG. 14, 117; 424/70, 312, 365

[56] References Cited

U.S. PATENT DOCUMENTS 4,148,762  4/1979  Koch et al. .................. 252/544
4,261,851  4/1981  Duke ........................ 252/174.21
4,306,997  12/1981  Oneto et al. ................ 252/541

Primary Examiner—John E. Kittle
Assistant Examiner—Robert A. Wax
Attorney, Agent, or Firm—Toren, McGeady and Stanger

[57] ABSTRACT

The invention relates to a personal care cleansing agent based on an aqueous solution of a mixture of special betaines and anionic compounds. It is a characteristic of the invention that the fatty acid monoglyceride is present in an amount of 2 to 35 weight percent based on the betaine. By the addition of partial fatty acid esters of glycerin, the aqueous solutions even of impurities of free betaines can be thickened particularly for the preparation of bath additives, hair shampoos and shower gels. At the same time, the skin compatibility of the preparations is improved and a certain emollient effect is achieved.

3 Claims, No Drawings

PERSONAL CARE CLEANSING AGENT

BACKGROUND OF THE INVENTION

1. Field of the Invention

The invention relates to a personal care cleansing agent based on an aqueous solution of a mixture of betaines and anionic compounds.

2. Description of the Prior Art

In particular, the use of combinations of certain betaines and anionic compounds as bath additives is known. For example, it is known to use:

(a) betaines of the general formula $$R^1 N^{\oplus} R^2 R^3 (CH_2)_y COO^{\ominus} \quad (I)$$

in which $R^1$ is an alkyl radical of a fatty acid with 6 to 18 carbon atoms or the $R^4 CONH(CH_2)_x$ radical, in which $R^4$ is an alkyl radical of a fatty acid with 6 to 18 carbon atoms, and $x = 2$ or $3$, $R^2$ and $R^3$ are the same or different and represent alkyl radicals with 1 to 4 carbon atoms and $y = 1, 2,$ or $3$, in combination with, (b) one or more anionic compounds from the group of sodium or ammonium alkyl ether sulfate, alkanolamine alkyl ether sulfate, alkanolamine alkyl sufate, in which the alkyl group has 8 to 14 carbon atoms, in a weight ratio of a:b from 3:7 to 7:3.

Betaines of formula I have been used for some time and, to an increasing extent, for the preparation of shower gels, hair shampoos, bath additives and similar cosmetic preparations.

For this purpose, betaines of the general formula $$R^5 \cdot CONH(CH_2)_n - \overset{\overset{\displaystyle R^6}{|}}{\underset{\underset{\displaystyle R^7}{|}}{N^{\oplus}}} - (CH_2)_m COO^{\ominus} \quad (II)$$

have proven themselves particularly useful. In these betaines, $R^5$ represents the alkyl radical of a fatty acid with 10 to 18 carbon atoms, $R^6$ and $R^7$ are the same or different and represent alkyl or hydroxyalkyl radicals with 1 to 4 carbon atoms, $n = 2$ or $3$, and $m = 1, 2, 3$ or $4$.

The use of such betaines as bath additives is described in German Patent 1,172,802. However, it turned out in practice that betaines of formula II can occasionally cause skin irritations, and especially irritations of the mucous membranes in people with sensitive skin.

A process was therefore developed as disclosed in German patent application No. P 29 26 479.7-42 wherein during the entire course of the reaction, the quaternization reaction is carried out in an alkaline solution which has a pH of 7.5 to 10, measured at 98° C. The betaines, so prepared, are essentially free of unreacted fatty acid amide dialkylamines and organically linked chlorine. The products show an improved mucous membrane compatibility.

Surprisingly, it has now turned out that these betaines, which are obtained in a purer form than those of the state of the art, cannot be thickened by conventional means, i.e., by the addition of anionic compounds, such as, sodium or ammonium alkyl ether sulfate, alkanolamine alkyl ether sulfate, or alkanolamine alkyl sulfate, in which the alkyl group has 8 to 14 carbon atoms.

For many application purposes, however, it is essential that the aqueous solutions of the betaines have an increased viscosity, especially, for example, for the preparation of shower gels or hair shampoos. The thickening of betaines of the general formula I, in which the $R^1$ is the alkyl radical of a fatty acid with 6 to 18 carbon atoms, also creates the same difficulties.

SUMMARY OF THE INVENTION

We have discovered a method for thickening aqueous solutions of betaines of the formula I, even when the betaines are present essentially in a pure form and, in particular, are free from skin-irritating impurities. This is accomplished by the addition of monoglycerides of fatty acids to the betaines. More specifically, the inventive personal care cleansing agent of the present invention contains monoglycerides of fatty acids, the fatty acid component having 8 to 18 carbon atoms and the minimum content of monoester being about 70 weight percent, in an amount of about 2 to 35 weight percent based on the betaine.

DESCRIPTION OF THE PREFERRED EMBODIMENT

Preferably, the inventive personal care cleansing agent contains glycerin monolaurate, with a minimum content of monoester of about 90 weight percent, in an amount of 2 to 24 weight percent based on the betaine.

In accordance with the invention, the concept of a fatty acid monoglyceride, whose fatty acid component has 8 to 18 carbon atoms, is defined as a partial glyceride of a fatty acid, which contains mono-, di- and triesters of the fatty acid, in which, however, the monoglyceride content is at least about 70 weight percent. Monoglycerides, whose fatty acid component has 8 to 12 carbon atoms are preferred. However, esters of longer-chain fatty acids up to 18 carbon atoms are also suitable. In this case, however, the unsaturated fatty acids, especially oleic acid, are preferred as the esterification component.

As used herein, the expression glycerin monolaurate includes not only the monoglyceride of lauric acid, but also, the monoglyceride of a mixture of fatty acids, which has 12 carbon atoms on the average. The naturally occurring mixture of fatty acids obtained by splitting fat, is particularly suitable.

Those skilled in the art accordingly have the option, in keeping with the teachings of the invention, to prepare aqueous solutions of moderately increased viscosity as well as gels of high consistency and therefore, to adapt the preparation to the intended use. In so doing, it was surprising that monoglycerides of fatty acids could be mixed with the aqueous surfactant solutions in the required amount, since such mixing with solutions of other amphoteric surfactants frequently leads to separation.

Moderately thickened solutions may be used with particular advantage as, for example, bath additives or shampoos. Gels, on the other hand, are more suitable as personal care cleansing agents for the shower. The preparations can also be used as liquid soaps, in which case the viscosity of the soap solution can be adapted to the metering delivery device.

In addition, it surprisingly turned out that the mucous membrane compatibility of the aqueous betaine solutions could be improved even further by the addition of fatty acid monoglycerides, so that the fatty acid monoglycerides not only have a thickening effect, but also improve the compatibility. In addition, there was a distinct emollient effect which depends on the concentration of fatty acid monoglyceride added.

The invention preparations can be mixed with the usual manufacturing materials, such as, for example, dyes, perfumery oils, preservatives and other additional skin-care substances, and converted into the proper form as requested by the customer.

In the following table, various formulations in accordance with the present invention, and their viscosities in mPas are given.

TABLE I

| Betaine Weight-% and Type | Anionic Components Type | Anionic Components Number of carbon atoms in the alkyl radical | Weight-% | Water Weight-% | Monoglyceride Number of carbon atoms in the fatty acid radical | Monoglyceride content | Weight % | Viscosity of the Preparation mPas 20° C. |
|---|---|---|---|---|---|---|---|---|
| 7.1 I | A | 12 | 7.0 | 84.5 | 12 | 90% | 1.4 | 50,000 |
| 8.5 I | A | mixture of 12 to 14 | 5.0 | 84.9 | 12 | 90% | 1.6 | 21,000 |
| 7.1 I | A | mixture of 12 to 16 | 5.8 | 85.7 | 12 | 90% | 1.4 | 24,000 |
| 7.1 I | A | 12 | 7.0 | 84.5 | mixture of 8 to 18* | 80% | 1.4 | 47,000 |
| 7.1 I | A | 12 | 7.0 | 84.5 | mixture of 8 to 18** | 90% | 1.4 | 30,000 |
| 7.1 I | A | 12 | 7.0 | 84.5 | 18*** | 90% | 1.4 | 46,000 |
| 7.1 I | A | 12 | 7.0 | 84.5 | 12 | 70% | 1.4 | 20,000 |
| 7.1 I | B | 12 | 12.5 | 79.0 | 12 | 90% | 1.4 | 45,000 |
| 4.5 II | A | 12 | 9.8 | 84.9 | 12 | 90% | 0.8 | 90,000 |

The symbols and abbreviations used in Table I are explained as follows:

Betaine Type I corresponds to formula I in which the indexes have the following meaning:
$R^4$ = alkyl radical with 6 to 18 carbon atoms,
$R^2$ and $R^3$ = methyl radicals
$x = 3$
$y = 1$.

Betaine Type II corresponds to formula I in which the indexes have the following meaning:
$R^1$ = alkyl radical with 14 to 16 carbon atoms
$R^2$ and $R^3$ = methyl radicals
$y = 1$
A = sodium alkyl ether sulfate
B = triethanolamine lauryl sulfate.
* = fatty acid component from coconut oil
** = fatty acid component from hydrogenated oil
*** = fatty acid component of oleic acid.

I claim:
1. An aqueous solution of a mixture of:
(a) betaines having the formula

$$R^1N^{\oplus}R^2R^3(CH_2)_yCOO^{\ominus}$$

in which
$R^1$ is an alkyl radical of a fatty acid with 6 to 18 carbon atoms or the $R^4CONH(CH_2)_x$ radical, in which $R^4$ is an alkyl radical of a fatty acid with 6 to 18 carbon atoms, and
$x = 2$ or $3$,
$R^2$ and $R^3$ are the same or different and represent alkyl radicals with 1 to 4 carbon atoms and
$y = 1$, $2$, or $3$;
(b) one or more anionic compounds selected from the group consisting of sodium or ammonium alkyl ether sulfate, alkanolamine alkyl ether sulfate, and alkanolamine alkyl sulfate, wherein the alkyl group has 8 to 14 carbon atoms; and
the weight ratio of a:b being about from 3:7 to 7:3,
(c) monoglycerides of fatty acids, the fatty acid component having from 8 to 18 carbon atoms and the minimum content of monoester being about 70 weight percent,
the amount of monoglycerides being from about 2 to 35 weight percent based on the amount of betaine.

2. The solution of claim 1 which contains glycerin monolaurate with a minimum monoester content of about 90 weight percent in an amount of from about 2 to 24 weight percent based on the betaine.

3. The solution of claim 1 wherein the amount of mixture is from about 14.3 to 21.6 weight percent based on the total amount of water and mixture.

* * * * *